United States Patent [19]
Klieman

[11] Patent Number: 5,171,253
[45] Date of Patent: Dec. 15, 1992

[54] VELCRO-LIKE CLOSURE SYSTEM WITH ABSORBABLE SUTURE MATERIALS FOR ABSORBABLE HEMOSTATIC CLIPS AND SURGICAL STRIPS

[76] Inventor: Charles H. Klieman, 79 Cypress Way, Rolling Hills Estates, Calif. 90274

[21] Appl. No.: 673,597
[22] Filed: Mar. 22, 1991
[51] Int. Cl.⁵ ............................................ A61B 17/00
[52] U.S. Cl. .................................... 606/158; 606/157; 128/DIG. 15; 24/446
[58] Field of Search ............... 128/DIG. 15; 606/157, 606/158, 203; 24/445, 446

[56] References Cited

U.S. PATENT DOCUMENTS

| | | | |
|---|---|---|---|
| D. 308,465 | 6/1990 | Hieffer | 128/DIG. 15 |
| 3,746,002 | 7/1973 | Haller | 606/207 |
| 4,672,722 | 6/1987 | Malamed | 128/DIG. 15 |
| 4,821,719 | 4/1989 | Fogarty | 606/158 |
| 4,821,720 | 4/1989 | Hajduch | 606/157 |
| 4,844,066 | 7/1989 | Stein | 606/158 |
| 5,002,522 | 3/1991 | Casey | 606/157 |

Primary Examiner—Stephen C. Pellegrino
Assistant Examiner—Gary Jackson
Attorney, Agent, or Firm—Spensley Horn Jubas & Lubitz

[57] ABSTRACT

Hemostatic clips and surgical strips made of deformable and preferably absorbable material have opposite elongate portions readily locked or secured together when clamped over a vessel or other bodily part. The elongate portions have opposite facing surfaces provided with a plurality of flexible members comprised of Velcro-like or similar entangling configurations, which become entangled when the surfaces are pressed together over the vessel or other bodily part. Other configurations include one or more strips of deformable material having surfaces provided with flexible members capable of entanglement to form clips or bands useful in a variety of different surgical procedures.

11 Claims, 2 Drawing Sheets

VELCRO-LIKE CLOSURE SYSTEM WITH ABSORBABLE SUTURE MATERIALS FOR ABSORBABLE HEMOSTATIC CLIPS AND SURGICAL STRIPS

BACKGROUND OF THE INVENTION

1. Field of the Invention

The present invention relates to absorbable suture materials formed into strips and hemostatic clips, for closing off tubular members such as veins, arteries or other blood vessels and fluid ducts during surgical procedures, and for support of nerves, vessels, bones and other anatomical structures. It encompasses different configurations of the absorbable suture materials using a basic closure mechanism.

2. History of the Prior Art

It is well known that during many surgical procedures hemostatic clips are used for strangulation or closure of blood vessels and fluid ducts. Traditionally, the vessel was clamped with a hemostat, following which a ligature was secured about the vessel to provide closure and to permit removal of clamps. This procedure was cumbersome and time consuming.

As a result, various different improved hemostatic clips have evolved which replace the aforementioned procedure with a simpler method of vessel ligation. An example of such an improved hemostatic clip is provided by U.S. Pat. No. 4,188,953 of Charles H. Klieman and Richard M. Densmore, which patent issued Feb. 19, 1980. The Klieman, et al. patent describes a hemostatic clip of elongate deformable material with a pair of arms having flat opposing surfaces with diagonal recesses therein. The recesses in the opposing surfaces are arranged so as to be angularly displaced with respect to one another, so that when the surfaces are brought into contact the recesses on opposing surfaces form a crosshatched pattern. The arms are substantially longer than the bail portion which joins them together at the base of the generally U-shaped configuration to provide stability of the clip within the clip applicator. Each arm has a generally trapezoidal cross-section with a narrower outer portion adapted to be received in a respective groove of the clip applicator. The bail portion is generally V-shaped in cross-section.

The hemostatic clips described in the Klieman, et al. patent have proven to be highly advantageous compared with prior art hemostatic clip designs. The clips of the Klieman, et al. patent are typically made of biologically inert materials such as titanium, tantalum and stainless steel, but may also be made of absorbable materials which are slowly absorbed by the body. However, as successful as such clips are when made of deformable metal such as tantalum, problems frequently arise in the closure system of absorbable clips due to the physical properties of absorbable materials. As a result, clips made of absorbable material have been designed to lock at their tip in order to assure their closure. They are therefore bulkier, and need to be placed completely around the vessel to allow closure at the tip.

There is therefore a need for an improved closure system for absorbable surgical and suture materials. It would be advantageous to provide absorbable strip materials capable of being formed or cut in various sizes to form clips, bands, cuffs and other configurations useful in various different surgical procedures. This improved closure system for absorbable materials would be capable of use for both hemostatic clips and for a multitude of other applications, when configured as strips.

BRIEF DESCRIPTION OF THE INVENTION

Hemostatic clips according to the invention have opposite elongate portions which are readily locked or secured together when clamped over a vessel, even when made of flexible, deformable material which is readily absorbable. The elongate portions of such clips have opposite facing surfaces provided with a plurality of flexible members which become entangled with one another when such surfaces are pressed together over a vessel to clamp the vessel shut. The flexible members which may be of any appropriate configuration for entanglement upon contact may be formed in the manner of the well known "Velcro" design in which one surface is comprised of flexible members formed into loops with an opposing surface comprised of flexible members formed into hooks for entanglement with the loops. Alternatively, the loops and hooks can be formed on the same surface.

In a preferred embodiment of a hemostatic clip according to the invention, the clip is of generally U-shaped configuration having a bailing portion at the base of the U-shaped configuration with a pair of opposite arms extending outwardly from opposite ends of the bailing portion. The arms have facing surfaces provided with the flexible members for entanglement to lock the arms together over a vessel being closed. The bailing portion also has opposite facing surfaces provided with the flexible members.

The hemostatic clip can be comprised of a base member of generally U-shaped configuration having a thin layer of material mounted on an inside surface thereof. The thin layer has a surface opposite the base member which is comprised of the flexible members, with the base member and the thin layer of material together forming the bailing portion and the pair of arms. In an alternative arrangement, the clip is comprised of a single integral member of generally U-shaped configuration forming the base portion and the pair of arms.

Because the two arms approximate easily and securely using such materials in accordance with the invention, it is possible to provide clips which are not attached at the bail end. Two separate strips, one containing the hooks and one the loops, or a single strip containing both, can be applied together to effect the same result.

Also, strips of the absorbable material and having surfaces provided with Velcro-like fastening configurations can be made in various sizes for uses other than as hemostatic clips. Thus, a band formed from one or more such strips can be used to suspend the bladder, can be placed around a vascular anastomosis, can be incorporated with other implant devices such as pacemaker leads, or orthopedic devices, can be used to immobilize a severed nerve, vessel, bone or ligament, and can be used in other such surgical situations.

BRIEF DESCRIPTION OF THE DRAWINGS

The foregoing and other objects, features and advantages of the invention will be apparent from the following more particular description of preferred embodiments of the invention, as illustrated in the accompanying drawings, in which.

DETAILED DESCRIPTION

Figure 1:
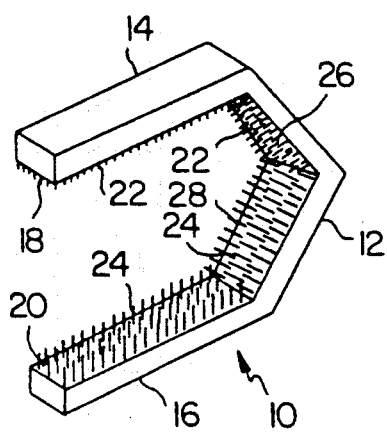
FIG. 1 is a perspective view of an absorbable hemostatic clip in accordance with the invention.

FIG. 1 shows an absorbable hemostatic clip 10 according to the invention. The clip 10 is of generally U-shaped configuration and includes a bail portion 12 at the base of the generally U-shaped configuration and a pair of opposite arms 14 and 16 extending outwardly from opposite ends of the bail portion 12 to form the opposite sides of the generally U-shaped configuration. The clip 10 is preferably made of absorbable material such as PDS (polydioxinone), alone or in combination with other absorbable materials but may be made of any material which is deformable.

In accordance with the invention, the arms 14 and 16 have opposite facing inside surfaces 18 and 20 thereof, respectively, which are provided with a plurality of flexible members 22 and 24, respectively. The flexible members 22 and 24 are designed so as to entangle with one another when the surfaces 18 and 20 are pressed together. The bail portion 12 also has opposite facing inner surfaces 26 and 28. The surface 26 is covered with the flexible members 22, and the surface 28 is covered with the flexible members 24. The flexible members 22 and 24 on the surfaces 26 and 28 entangle when the surfaces 26 and 28 are pressed together.

The flexible members 22 and 24 on the surfaces 18, 20, 26 and 28 can be of any appropriate configuration which provides entanglement of the members on the opposing surfaces upon contact. One appropriate configuration is that used in the well known "Velcro" design, in which one surface is provided with flexible members in the form of loops with the opposing surface being covered by flexible members in the form of hooks. In the clip 10 of FIG. 1, the flexible member 22 on the surfaces 18 and 26 can be formed into loops with the flexible members 24 on the surfaces 20 and 28 being formed into hooks, and vice versa. Alternatively, the flexible members 22 and 24 can comprise combinations of loops and hooks or other shapes suitable for entanglement to provide secure joinder.

Figure 2:
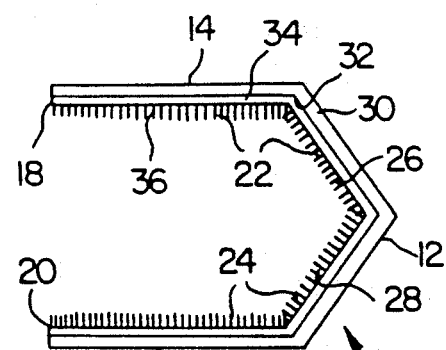
FIG. 2 is a side view of the clip of FIG. 1 showing one particular construction thereof in accordance with the invention.

FIG. 2 shows one construction arrangement of the clip 10 in which a base member 30 of thin, flat configuration extends along the entire length of the clip 10 including the bail portion 12 and the arms 14 and 16. The base member 30 has an inner surface 32 thereof on which a relatively thin layer 34 is mounted. The thin layer 34 has a surface 36 opposite the inner surface 32 of the base member 30 which includes the flexible members 22 and 24. The base member 30 and the thin layer 34 can be made of like or different materials. Preferably, both are made of absorbable material.

Figure 3:
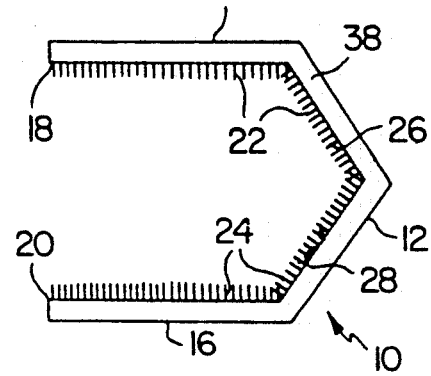
FIG. 3 is a side view of the clip of FIG. 1 showing another construction thereof in accordance with the invention.

In an alternative construction arrangement as shown in FIG. 3, the entire clip 10 including the bailing portion 12, the arms 14 and 16 and the flexible members 22 and 24 are comprised of a single integral member 38. The member 38 can be made of any appropriate material, with absorbable material being preferred.

Figure 4:
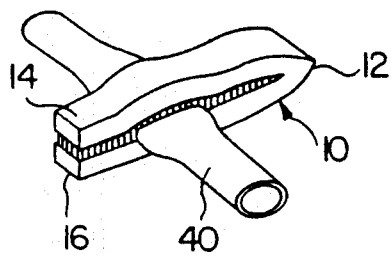
FIG. 4 is a perspective view showing the manner in which the clip of FIG. 1 may be used to clamp over and close or strangle a vessel.

FIG. 4 shows the clip 10 after it has been clamped over a vessel 40. The clip 10 is clamped over the vessel 40 manually or by using an applicator having opposite pivoting portions which receive the opposite arms 14 and 16. Closure of the pivoting applicator deforms the clip 10 so as to bring the opposite arms 14 and 16 thereof and the opposite surfaces 22 and 24 of the bail portion 12 thereof together over the vessel 40. The portions of the flexible members 22 and 24 on opposite sides of the vessel 40 entangle as the facing surfaces 18 and 20 of the arms 14 and 16 and the surfaces 22 and 24 of the bailing portion 12 are forced together. Such entanglement holds the clip 10 in the clamped position shown in FIG. 4, upon removal of the applicator. The clip 10 may be left in place following completion of the surgical procedure.

Figure 5:
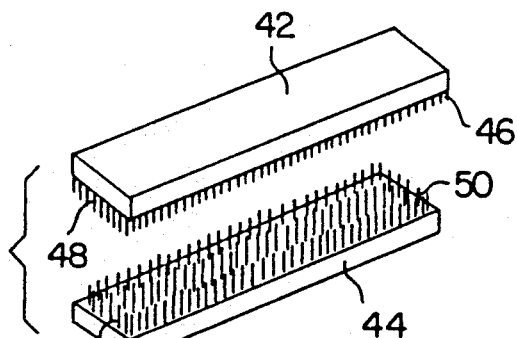
FIG. 5 is a perspective view of a pair of strips in accordance with the invention which can be joined to form a clip or which can be used for other surgical applications.

FIG. 5 shows a further alternative embodiment in accordance with the invention. In the embodiment of FIG. 5, two different strips 42 and 44 of approximately equal length are provided. The strips 42 and 44 are made of flexible material similar to the materials used for the clips 10 of FIGS. 1–4. Preferably, the material of the strips 42 and 44 is absorbable.

The strip 42 has flexible members 46 extending from a lower surface 48 thereof. The strip 44 has flexible members 50 extending from an upper surface 52 thereof. The flexible members 46 can be in the form of loops with the flexible members 50 being in the form of hooks. Alternatively, the flexible members 46 and 50 can each comprise a combination of loops and hooks or other shapes suitable for entanglement to provide secure joinder thereof. For convenience, the strips 42 and 44 can be cut from a single strip or roll of such material.

Figure 6:
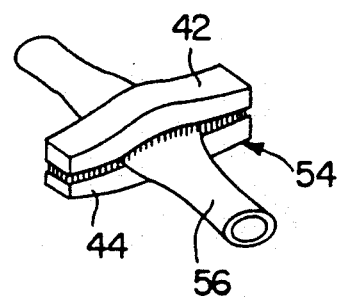
FIG. 6 is a perspective view showing the manner in which the pair of strips of FIG. 5 may be used as a clip to clamp over and close or strangle a vessel.

FIG. 6 shows the strips 42 and 44 as they are employed to form a hemostatic clip 54 over a vessel 56. The opposite strips 42 and 44 function much in the same manner as the clip 10 shown in FIG. 4, except that they are not joined together at one end and have no bail portion. Nevertheless, the strips 42 and 44 function to form the clip 54 in an effective manner. This is principally due to the fact that the flexible members 46 and 50 at the opposite ends of the strips 42 and 44 entangle with a substantial amount of resistance to separation.

The ability to form strips of different sizes such as the strips 42 and 44 shown in FIGS. 5 and 6 provides for the makeup of bands from one or more such lengths. Such bands are useful in a variety of different surgical applications and procedures.

Figure 7:
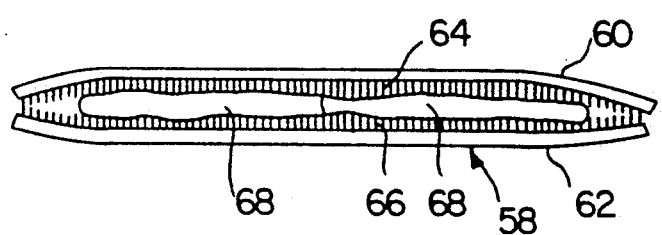
FIG. 7 is a side view of a pair of strips similar to those of FIG. 5 and showing the manner in which such strips form a band which can be used to secure a nerve, ureter, bone or vessel.

FIG. 7 shows a band 58 comprised of opposite strips 60 and 62. As in the case of the strips 42 and 44 of FIGS. 5 and 6, the strips 60 and 62 are provided with flexible members 64 and 66 at the facing surfaces thereof which are capable of entanglement with one another. As in the case of the strips 42 and 44, the flexible members 64 and 66 of the strips 60 and 62 can be comprised of loops and hooks respectively, or alternatively may comprise combinations thereof.

As shown in FIG. 7, the opposite strips 60 and 62 are joined together by the flexible members 64 and 66 at the opposite ends thereof so as to secure a member 68 therebetween. The member 68 may comprise any one of various different bodily parts such as a nerve, bone, vessel or a ureter.

Band arrangements such as the band 58 shown in FIG. 7 can be used in a variety of different surgical applications, as previously noted. Such bands can, for example, be used to hold the ends of severed nerves together in proper orientation during a reparative procedure and during the subsequent healing time. In the field of urology, such bands can be used to hold the bladder neck fixated to the pubis for urinary suspension, or to hold the ends of a severed ureter together during the healing time and to relieve tension on the suture line.

In the field of orthopedics, such bands can be used to fixate small broken bones by approximating the bones with opposite strips. This avoids leaving metal wires and screws in place would have to be removed at a later date.

In the cardiovascular field, such bands can be used to remove from graft and vessel anastomosis and to approximate the ends of severed vessels.

Further uses include ligature strips to tie off larger arteries and aneurysms, as x-ray markers when combined with a radiopaque substance, as fixation strips for sternal approximation, and as ligature strips to stop bleeding from a torn spleen or liver. Still other uses of the bands include the combination thereof with other devices such as metallic orthopedic devices for fixation, the combination thereof with hemostatic and bacteriostatic agents to provide long acting release of the drugs at a particular site, for fixation of pacemaker leads at their tip, to replace dacron cuffs in hyperalimentation catheters to allow easy removal of the catheters nonsurgically, and as a new type of suture.

Figure 8:
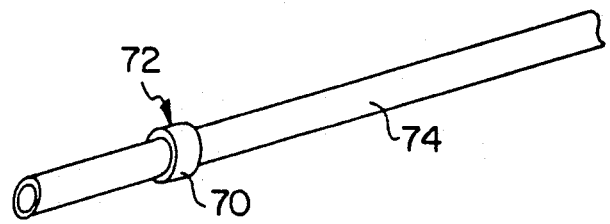
FIG. 8 is a perspective view of a catheter with a strip of material according to the invention forming a cuff thereon.

FIG. 8 illustrates an arrangement in which a strip 70 is used to form a cuff 72 on a catheter 74. The strip 70 may be constructed in the manner of the strips 42 and 44 of FIGS. 5 and 6, and the strips 60 and 62 of FIG. 7. Also, the cuff 72 may have hooks and loops on one or both sides of the forming band.

While the invention has been particularly shown and described with reference to preferred embodiments thereof, it will be understood by those skilled in the art that changes in form and details may be made therein without departing from the spirit and scope of the invention.

What is claimed is:

1. Absorbable hemostatic clip apparatus of elongate deformable and absorbable material in a generally U-shaped configuration and having a bail portion and a pair of arms extending from opposite ends of the bail portion, the pair of arms having facing inner surfaces provided with flexible members, the flexible members on the facing surface on a first of the pair of arms entangling with the flexible members on the facing surface of a second of the pair of arms when the facing surfaces of the first and second arms are pressed together to hold the pair of arms together.

2. Hemostatic clip apparatus according to claim 1, wherein the bail portion has opposite portions with facing inner surfaces provided with the flexible members.

3. Hemostatic clip apparatus according to claim 1, wherein the flexible members on the facing surface of the first of the pair of arms are in the shape of loops and the flexible members on the facing surface of the second of the pair of arms are in the shape of hooks.

4. Hemostatic clip apparatus according to claim 1, wherein the flexible members on the facing surfaces of the first and second arms are each comprised of a combination of loop and hook shapes.

5. Hemostatic clip apparatus according to claim 1, wherein the clip apparatus is comprised of an absorbable base member of generally U-shaped configuration and a thin layer of absorbable material mounted on an inside surface of the base member and having a surface opposite the base member which is comprised of the flexible members, the base member and the thin layer of absorbable material together forming the bail portion and the pair of arms.

6. Hemostatic clip apparatus according to claim 1, wherein the clip apparatus is comprised of a single integral member of generally U-shaped configuration forming the bail portion and the pair of arms.

7. An elongated deformable strip of absorbable material for use in surgical procedures and having at least one surface thereof provided with flexible entanglement elements of absorbable material.

8. An elongated deformable strip according to claim 7, wherein some of the entanglement elements are in the shape of loops and other ones of the entanglement elements are in the shape of hooks.

9. Absorbable apparatus for securing at least one bodily part therein comprising a pair of opposite strips of deformable and absorbable material, the strips having facing surfaces provided with flexible members, the flexible members on the facing surface of the first strip entangling with the flexible members on the facing surface of the second strip when the facing surfaces of the first and second strips are pressed together to hold the first and second strips together.

10. Apparatus according to claim 9, wherein the flexible members on the facing surface of the first strip are in the shape of loops and the flexible members on the facing surface of the second strip are in the shape of hooks.

11. Apparatus according to claim 9, wherein the flexible members on the facing surfaces of the first and second strips are each comprised of a combination of loops and hooks.

* * * * *